(12) United States Patent
Kramp et al.

(10) Patent No.: US 7,133,492 B2
(45) Date of Patent: Nov. 7, 2006

(54) METHOD FOR REDUCING RADIATION EXPOSURE DURING PATIENT POSITIONING

(75) Inventors: George Kramp, Elmhurst, IL (US); John Baumgart, Hoffman Estates, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 11/091,993

(22) Filed: Mar. 29, 2005

(65) Prior Publication Data

US 2005/0220274 A1    Oct. 6, 2005

Related U.S. Application Data

(60) Provisional application No. 60/557,494, filed on Mar. 30, 2004.

(51) Int. Cl.
   *G01N 23/04* (2006.01)

(52) U.S. Cl. .......................... 378/62; 378/42; 378/150
(58) Field of Classification Search ............... 378/42, 378/62, 98.2, 98.5, 147, 150, 151, 195, 196, 378/197
See application file for complete search history.

(56) References Cited

U.S. PATENT DOCUMENTS

| | | | | |
|---|---|---|---|---|
| 4,833,625 | A * | 5/1989 | Fisher et al. | 345/668 |
| 5,090,401 | A | 2/1992 | Schwieker | |
| 5,278,887 | A * | 1/1994 | Chiu et al. | 378/156 |
| 5,282,254 | A * | 1/1994 | Chiu et al. | 382/132 |
| 5,287,396 | A * | 2/1994 | Stegehuis | 378/98.2 |
| 5,369,678 | A * | 11/1994 | Chiu et al. | 378/62 |
| 5,394,455 | A * | 2/1995 | Roeck et al. | 378/98.3 |
| 6,463,121 | B1 * | 10/2002 | Milnes | 378/62 |
| 6,614,877 | B1 * | 9/2003 | Anderton | 378/98.7 |
| 2003/0018245 | A1 | 1/2003 | Kaufman et al. | |

* cited by examiner

*Primary Examiner*—Allen C. Ho

(57) ABSTRACT

A method of reducing radiation exposure by panning and zooming the first acquired image rather than using continuous radiation fluoroscopy.

2 Claims, 1 Drawing Sheet

METHOD FOR REDUCING RADIATION EXPOSURE DURING PATIENT POSITIONING

PRIORITY CLAIM TO RELATED APPLICATION

This application claims priority from U.S. Provisional Patent Application Ser. No. 60/557,494 filed on Mar. 30, 2004, the entire contents of which is herein incorporated by reference.

BACKGROUND OF THE INVENTION

1. Field of the Invention

This invention relates generally to x-ray imaging systems. More specifically, this invention relates to methods of managing workflow in imaging patients to reduce exposure to x-ray radiation.

2. Background and Prior Art

Digital x-ray imaging systems include C-arm volume imaging systems. Typically, these systems must be positioned with respect to a patient during a procedure. Typically, the imaging system will operate in a fluoroscopic mode during the movement between positions in order to correctly position the C-arm. This is an accurate way of determining position, but exposes the patient to continuous low level radiation during positioning.

In a current procedure, a user (such as a technician) will acquire a first image, then move the patient position to a second position determined by fluoroscopy during positioning. At the second position another image is acquired.

Accordingly, there remains a need in the art for a method to position a patient in an x-ray imaging system while minimizing radiation exposure in a clinical setting.

SUMMARY OF THE INVENTION

The fluoroscopic operation between primary exposures for patient positioning can be replaced by panning and zooming of a first acquired image.

BRIEF DESCRIPTION OF THE DRAWINGS

The present invention will become more fully understood from the detailed description given herein below and the accompanying drawings which are given by way of illustration only, and are not limitative of the present invention, and wherein.

DETAILED DESCRIPTION OF THE PREFERRED EMBODIMENTS

According to the present invention, a method for reducing radiation exposure of a patient during patient positioning during a radiographic procedure. Such procedures can include many forms of angiography.

Figure 1:
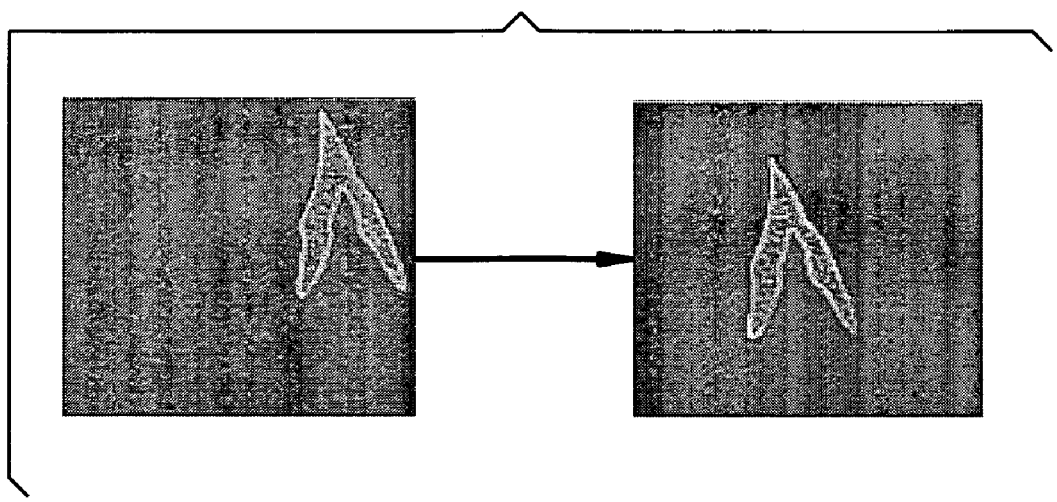
FIG. 1 is a view of panning the first acquired image.

In an embodiment of the current invention, the user acquires a first image. Then the user begins to move the patient table or C-cam. The first image itself is panned to the position of the next exposure (see FIG. 1). Note that if the image is panned off the screen then an arrow indicating the direction of the anatomy to be exposed is drawn.

Figure 2:
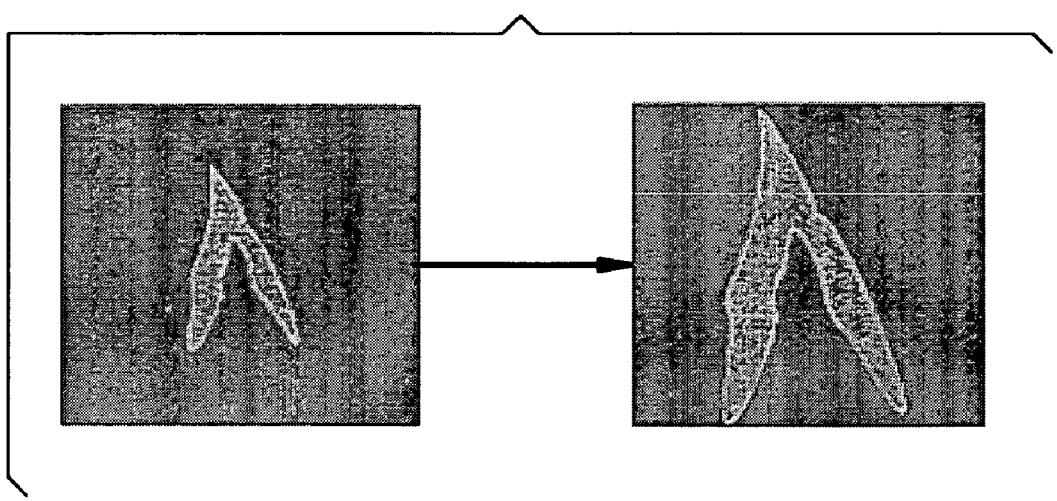
FIG. 2 is a view of zooming the second acquired image.

The user then adjusts the collimator blades (see FIG. 2). The displayed image is zoomed to fill the screen as the collimator is closed, or shrunk as the collimator is opened. Note that in a preferred embodiment the collimator graphics are still displayed at this point, since it is possible for the collimator to be non-square. As the collimator is opened or closed, note that the physical x-ray system including the detector and x-ray source, or "lab", will automatically determine the best image intensifier or detector zoom stage to use and change it when necessary. This eliminates the need to explicitly set the zoom stage.

The user takes the next exposure. The imaging system zooms the second acquired image using fractional bilinear interpolation such that the exposed anatomy fills the screen. Note that in a preferred embodiment the electronic shutter is still displayed at this point, since it is possible for the collimator to be non-square.

The invention having been thus described, it will be obvious to those skilled in the art that the same may be varied in many ways without departing from the spirit and scope of the invention.

What is claimed is:

1. A method for reducing the exposure of a patient to radiation during patient positioning in an x-ray imaging procedure with an x-ray imaging system having an x-ray source and an x-ray detector and a digital imaging system, comprising the steps of
   acquiring a first image;
   positioning the patient;
   panning the first image by the digital imaging system;
   adjusting collimator blades of a collimator;
   zooming the first image by the digital imaging system as the collimator is closed;
   shrinking the first image by the digital imaging system as the collimator is opened;
   automatically setting a best image intensifier zoom stage by the digital imaging system;
   automatically setting a best detector zoom stage by the digital imaging system;
   acquiring a second image; and
   zooming the second image using fractional bilinear interpolation by the digital imaging system such that an exposed anatomy of the patient fills a screen.

2. A method for reducing the exposure of a patient to radiation during patient positioning in an x-ray imaging procedure with an x-ray imaging system having an x-ray source and an x-ray detector and a digital imaging system, comprising the steps of
   acquiring a first image;
   positioning the patient;
   panning the first image by the digital imaging system;
   drawing an arrow indication if the image is panned off the screen;
   adjusting collimator blades of a collimator;
   zooming the first image by the digital imaging system as the collimator is closed;
   shrinking the first image by the digital imaging system as the collimator is opened
   automatically setting a best image intensifier zoom stage by the digital imaging system;
   automatically setting a best detector zoom stage by the digital imaging system;
   acquiring a second image; and
   zooming the second image using fractional bilinear interpolation by the digital imaging system such that an exposed anatomy of the patient fills a screen.

* * * * *